US010575828B2

(12) United States Patent
Dunlap et al.

(10) Patent No.: US 10,575,828 B2
(45) Date of Patent: Mar. 3, 2020

(54) ULTRASOUND CALIBRATION DEVICE

(71) Applicant: Brainlab AG, Munich (DE)

(72) Inventors: Edward Dunlap, Munich (DE); Uli Mezger, Kirchheim (DE); Jerome Vuillemin, Munich (DE)

(73) Assignee: Brainlab AG, Munich (DE)

( * ) Notice: Subject to any disclaimer, the term of this patent is extended or adjusted under 35 U.S.C. 154(b) by 535 days.

(21) Appl. No.: 15/501,331

(22) PCT Filed: Oct. 29, 2014

(86) PCT No.: PCT/EP2014/073205
§ 371 (c)(1),
(2) Date: Feb. 2, 2017

(87) PCT Pub. No.: WO2016/023599
PCT Pub. Date: Feb. 18, 2016

(65) Prior Publication Data
US 2017/0215848 A1 Aug. 3, 2017

(30) Foreign Application Priority Data

Aug. 14, 2014 (DE) .................... 20 2014 103 766 U

(51) Int. Cl.
*A61B 8/14* (2006.01)
*A61B 8/00* (2006.01)
*A61B 34/20* (2016.01)
*A61B 90/20* (2016.01)
(Continued)

(52) U.S. Cl.
CPC ............ *A61B 8/587* (2013.01); *A61B 8/4254* (2013.01); *A61B 8/481* (2013.01); *A61B 8/58* (2013.01);
(Continued)

(58) Field of Classification Search
CPC ......... A61B 8/58; A61B 8/4455; A61B 8/587; A61B 8/481; A61B 2034/2063; A61B 2034/2055; A61B 2034/207; G01S 7/5205
See application file for complete search history.

(56) References Cited

U.S. PATENT DOCUMENTS 4,989,446 A * 2/1991 Conti ...................... A61B 8/06
73/1.16
6,138,495 A * 10/2000 Paltieli ................... A61B 8/587
73/1.86
(Continued)

FOREIGN PATENT DOCUMENTS

JP      2014-124319 A    7/2014
PL          219645 B1    5/2011
(Continued)

OTHER PUBLICATIONS

International Search Report prepared by INPI, Republique Francaise, FR1552803, dated Apr. 20, 2018, corresponding to PCT/2014/073205, pp. 1-5. France.
(Continued)

*Primary Examiner* — Mallika D Fairchild
(74) *Attorney, Agent, or Firm* — Tucker Ellis LLP

(57) ABSTRACT

The present invention relates to an ultrasound calibration device comprising a body portion having at least one echogenic fiducial; a marker portion having at least one tracking marker which can be detected by a medical tracking system; and a hook-shaped mounting portion extending from the body portion.
The present invention also relates to a method for calibrating an ultrasound probe, comprising the steps of filling a container with a fluid, in particular a physiologic salt solution; placing an ultrasound calibration device in accordance with the invention into the container; comparing, with the aid of a medical navigation system, a calculated position of at least
(Continued)

one fiducial with a determined position of the at least one fiducial which is determined using a tracked ultrasound probe.

17 Claims, 2 Drawing Sheets

(51) Int. Cl.
  *G01S 7/52* (2006.01)
  *A61B 8/08* (2006.01)
  *A61B 90/00* (2016.01)

(52) U.S. Cl.
  CPC .............. *A61B 34/20* (2016.02); *A61B 90/20* (2016.02); *G01S 7/5205* (2013.01); *A61B 8/4455* (2013.01); *A61B 2034/207* (2016.02); *A61B 2034/2055* (2016.02); *A61B 2034/2063* (2016.02); *A61B 2090/3925* (2016.02); *A61B 2090/3983* (2016.02)

(56) References Cited

U.S. PATENT DOCUMENTS

| | | |
|---|---|---|
| 2002/0035864 A1 | 3/2002 | Paltieli et al. |
| 2006/0036170 A1 | 2/2006 | Lachanine et al. |
| 2008/0287787 A1 | 11/2008 | Sauer et al. |
| 2009/0312641 A1 | 12/2009 | Kozak et al. |
| 2012/0275645 A1 | 11/2012 | Koenig et al. |
| 2012/0277585 A1 | 11/2012 | Koenig et al. |
| 2014/0031664 A1 | 1/2014 | Kang et al. |

FOREIGN PATENT DOCUMENTS

| | | |
|---|---|---|
| WO | 99/33394 A1 | 7/1999 |
| WO | 2005/084551 A2 | 9/2005 |
| WO | 2009063360 A1 | 5/2009 |
| WO | 2009071503 A1 | 6/2009 |

OTHER PUBLICATIONS

Intellectual Property Office (IPO), Search report for GB1507554.2, date of search Sep. 28, 2015, p. 1. South Wales,UK.

Intellectual Property Office (IPO), Office action for GB1507554.2, date of report Oct. 2, 2015, pp. 1-6 South Wales, UK.

Intellectual Property Office (IPO), Office action for GB1507554.2, date of report Sep. 8, 2016, pp. 1-2 South Wales, UK.

European Patent Office (EPO), Written Opinion of the International Searching Authority for PCT/EP2014/073205, pp. 1-7,NL.

European Patent Office (EPO), International Search Report for PCT/EP2014/073205, dated Apr. 14, 2015, pp. 3, NL.

* cited by examiner

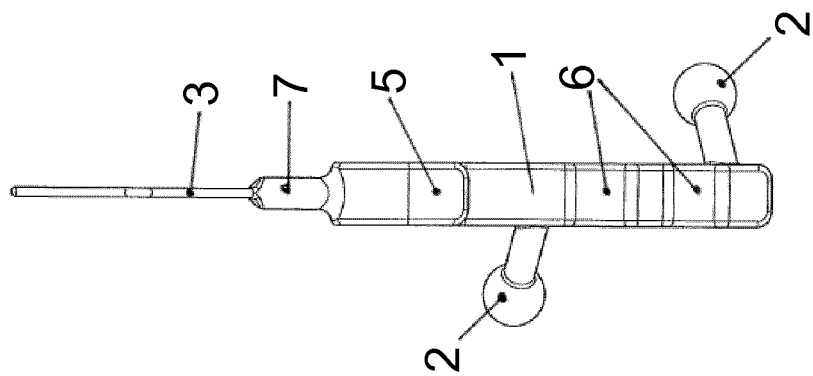
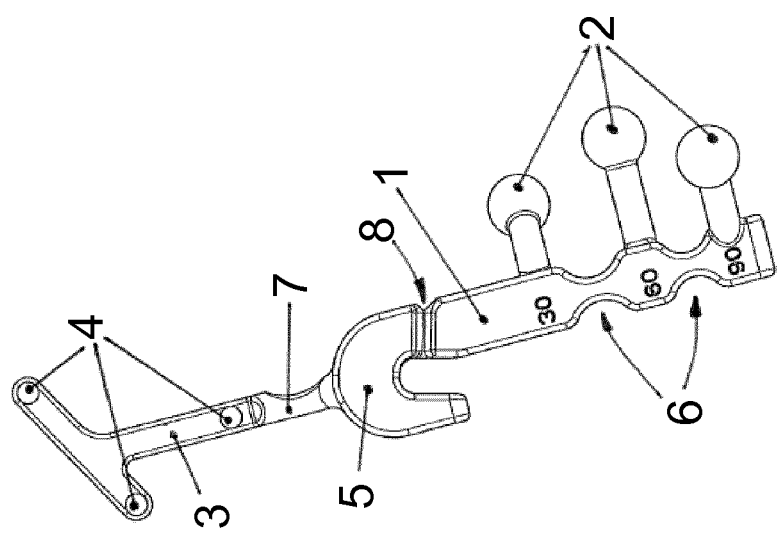
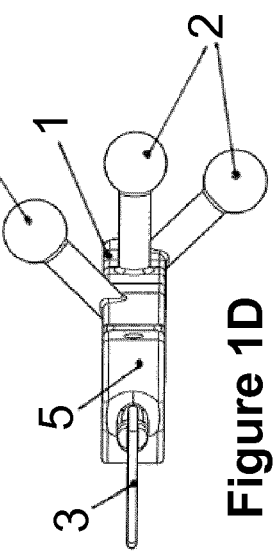
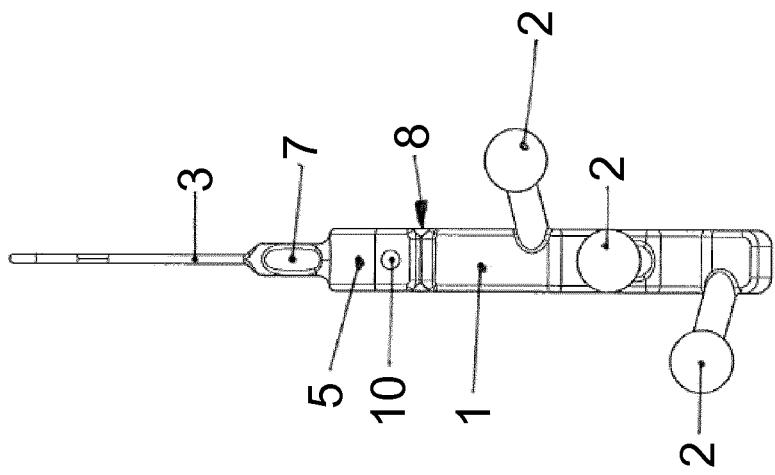

ULTRASOUND CALIBRATION DEVICE

RELATED APPLICATION DATA

This application is a national phase application of International Application No. PCT/EP2014/073205 filed Oct. 29, 2014 published in the English language.

The present invention relates to an ultrasound calibration device for calibrating the signal of an ultrasound probe and to a corresponding method for calibrating an ultrasound probe.

It is known from the prior art that ultrasound calibration devices, so-called ultrasound phantoms, can be used to calibrate ultrasound probes. For this purpose, such a phantom comprises a housing containing one or more echogenic fiducials such as wires which are visible to the ultrasound probe. The housing also contains an anechoic medium in which the fiducials are embedded and which conducts the ultrasound waves. As soon as the relative position of the fiducials and the ultrasound probe has been ascertained, for example by determining the spatial position of tracking markers attached to the phantom and to the probe, it is possible to verify the correct position of the fiducials as seen in the ultrasound image.

WO 2009/063360 discloses a generic ultrasound phantom comprising a container or tank filled with a liquid gel or other suitable aqueous medium, wherein a calibration feature/fiducial is immersed in the medium.

The use of current ultrasound phantoms is cumbersome, since the known phantoms are heavy (in part due to the anechoic medium contained within them) and need to be draped for reasons of sterility. The anechoic medium within the phantom can also dry out. In addition, the calibration depth available depends on the phantom size and is often limited to a few centimetres.

It is an object of the present invention to provide an ultrasound calibration device and a corresponding method for calibrating an ultrasound probe which overcome at least one of these problems.

This object is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The ultrasound calibration device, in one embodiment of the present invention, comprises:
- a body portion having at least one echogenic fiducial;
- a marker portion having at least one tracking marker which can be detected by a medical tracking system; and
- a hook-shaped mounting portion extending from the body portion.

In other words, the phantom in accordance with the present invention may comprise a body portion which provides support for one or more echogenic fiducials comprising an echogenic material such as echogenic plastic which can be detected by an ultrasound probe and therefore seen in an ultrasound image. If the body portion is made from an anechoic/sonolucent material, the at least one echogenic fiducial can be embedded within the body portion. In another embodiment, however, the fiducials can be provided on the outside of the body portion or even at a distance from the body portion by means of connecting members which hold the fiducials in a spatially fixed arrangement relative to the body portion.

The fiducials can exhibit any conceivable shape suitable for ultrasound calibration, wherein different fiducials can even exhibit different shapes. In a preferred embodiment, however, all the fiducials have a spherical shape which therefore appears the same even in ultrasound images taken from different directions.

The calibration device in accordance with the invention may also comprise a marker portion which bears one or more tracking markers, the spatial position of which can be determined by means of a medical tracking system, for example an optical tracking system, an ultrasound tracking system or an EM tracking system. Since the tracking markers are fixedly attached to the body portion via the marker portion, the spatial position of the fiducials can be determined at any point in time with the aid of the medical tracking system.

The calibration device in accordance with the invention can also have a hook-shaped mounting portion which extends from the body portion and allows the calibration device to be mounted or hooked onto the upper rim of any cup-shaped receptacle, such that the body portion together with the at least one fiducial extends at least partially into the receptacle.

The present invention recognises that cup-shaped receptacles and media exhibiting sonolucent properties (such as for example sterile isotonic water) are already available in a medical environment, such that it is possible to utilise these items by integrating them into a calibration procedure for an ultrasound probe. In other words, the invention provides an ultrasound phantom which omits all the parts which are available in a medical environment anyway and need not be provided as an integral part of the ultrasound probe. Specifically, the enclosed housing of a prior-art ultrasound phantom can be replaced with any suitable receptacle available, such as a glass, bowl or cup, and the anechoic medium encapsulated by the enclosed housing of prior-art phantoms can be replaced with any sonolucent material, such as sterile isotonic water with which the receptacle is filled. The phantom in accordance with the invention merely needs to provide one or more spatially detectable fiducials which, when submerged in the sonolucent media, allow an ultrasound probe to be calibrated.

In accordance with another embodiment of the present invention, the mounting portion has an opening which points substantially in a direction along the side of the body portion.

As already explained above, at least part of the body portion has to extend into a receptacle provided, such that the at least one echogenic fiducial is submerged in the sonolucent medium with which the receptacle is to be filled. For this purpose, the hook-shaped mounting portion has to be positioned relative to the body portion such that when the mounting portion is hooked onto the upper rim of the receptacle, the body portion extends downwards into the receptacle.

If the body portion has an elongated shape, the opening of the hook-shaped mounting portion should face downwards along the side of the body portion and in a direction substantially parallel to the longitudinal axis of the body portion.

In accordance with another preferred embodiment of the present invention, the body portion has a longitudinal shape, wherein a plurality of echogenic fiducials can, but need not, be successively arranged along the side of the body portion. Such an arrangement of the fiducials can for example conceivably allow an ultrasound probe to be calibrated for different depths, since fiducials can be arranged at different depths below the level of the echogenic medium in accordance with the length of the body portion extending into the receptacle. The fiducials can be fixedly coupled to the body portion via arms which extend in different spatial directions, such that the distance between the fiducials is increased for a given length of the body portion.

In accordance with a preferred embodiment, the body portion comprises at least one rated breaking feature between at least two of the fiducials. Breaking features such as breaking points or breaking lines, which can be formed by indentations, recesses, cut-outs, bores or openings and weaken the structure of the body portion to allow a part of the body portion to be broken off, enable the user to adapt the size of the calibration device to receptacles of different depths. If, for example, only a shallow receptacle is available, the user can break off some of the fiducials together with a part of the body portion, such that the remaining part of the body portion together with the remaining fiducials can be submerged within the shallow receptacle.

The calibration device in accordance with the invention can also comprise a dedicated handle portion which can be arranged between the mounting portion and the marker portion. It is often desirable to determine the so-called time delay of the ultrasound images (the discrepancy between the time an actual change in the position of structures detected by the ultrasound probe occurs and the time this positional change shows up in the ultrasound image), which requires the calibration device to be moved within the receptacle. Since the line of sight between the marker portion supporting the tracking markers and an optical tracking system must not be interrupted, and the user must be prevented from grasping the calibration device in the vicinity of the echogenic fiducials which might otherwise be disturbed, it is beneficial to provide a dedicated handle portion in order to indicate clearly to the user where to grasp the calibration device when moving it in order to determine the time delay.

The calibration device can be made from a plastic material, for example an echogenic plastic material, such that it can be provided as an inexpensive disposable item. Specifically, the calibration device can be injection-moulded. It is also possible to form the entire calibration device as one integral part, such that the body portion together with the fiducials, the marker portion and the mounting portion are injection-moulded as a single part. It is also conceivable for the body portion, the echogenic fiducials and/or the marker portion to constitute separate parts which are assembled to form the calibration device.

Alternatively, the marker portion can be attached to the body portion and/or to the mounting portion via a connection interface which allows the marker portion to be attached to the calibration device. For example, the body portion together with the fiducials and the mounting portion can be provided as an inexpensive disposable item, while the marker portion is provided as a reusable item which is connected to the body portion or to the mounting portion. The interface can be a clip fastener or any other suitable fastener which provides a positive fit or friction fit, wherein the interface can also allow the marker portion to be attached to the body portion and/or to the mounting portion in a single position only, such that the tracking markers are always arranged in a predetermined spatial position relative to the fiducials on the body portion.

In accordance with another embodiment, at least part of the calibration device exhibits an overall density which is substantially equivalent to a density of the sonolucent medium used, for example a physiologic salt solution. If the body portion which is to be submerged in a physiologic salt solution has neutral buoyancy, the body portion can be prevented from sinking or rising, such that the calibration device will maintain its position within the receptacle. For this purpose, the calibration device can also comprise at least one floating aid and/or at least one balance portion which enables a well-balanced calibration device to be achieved. The remaining parts which extend above the water level can also be balanced. Specifically, the centre of gravity of the remaining parts can be substantially on a vertical plane which includes the contact point or contact line between the mounting portion and the upper rim of a receptacle. In more general terms, the calibration device can be balanced around the contact point or contact line of the mounting portion such that the spatial position of the submerged body portion together with the fiducials is maintained.

The calibration device can also comprise a mark, preferably at a predetermined distance to the at least one fiducial, which indicates the extent to which the calibration device is to be submerged. If the body portion to be submerged in the sonolucent medium has neutral buoyancy, breaking off a part of the body portion will have no effect on the overall balance of the calibration device.

As already explained above, the calibration device can be a disposable item and thus provided as a pre-sterilised and packaged item.

The calibration device in accordance with the invention can also comprise a calibration feature in a predetermined position relative to the tracking markers. For example, an indentation can be formed in the calibration device, preferably in the body portion or the mounting portion. This indentation can aid in calibrating a tracked surgical device or instrument. Since the spatial position (spatial location and/or spatial orientation) of the indentation can be determined via the tracking system by detecting the position of the markers of the marker portion, the relative position of the indentation and the tracking markers attached to the instrument or device to be calibrated is also known. An instrument tip, for example, can be brought into contact with the indentation so as to determine the instrument's tip position relative to the instrument's tracking markers. In the same way, a focal point of a tracked medical microscope can be determined with respect to tracking markers of the microscope by focusing the microscope onto the indentation. The calibration feature can of course also exhibit any other suitable form, such as for example a groove, edge or extension.

Another aspect of the present invention relates to an ultrasound calibration system comprising a calibration device as explained above and a container/receptacle which is configured to be filled with a fluid and is shaped so as to accommodate the calibration device. Such a system allows an ultrasound calibration to be performed even if no suitable receptacle is readily available. The user merely has to fill the receptacle with a sonolucent medium, such as for example sterile isotonic water, and attach the calibration device to the upper rim of the receptacle. The calibration device can be provided together with the receptacle in a pre-sterilised package or can be provided separately. The receptacle can be made of a plastic material and/or can be a disposable item.

Another aspect of the present invention relates to a method for calibrating an ultrasound probe, comprising the steps of:
- filling a container with a fluid, in particular a physiologic salt solution;
- placing an ultrasound calibration device as described herein into the container;
- comparing, with the aid of a medical navigation system, a calculated position of at least one fiducial—which is calculated using a virtual model of the calibration device and a tracking system which detects the spatial position of the at least one tracking marker—with a determined position of the at least one fiducial which is determined using a tracked ultrasound probe.

To perform the calibration method in accordance with the invention, medical personnel can fill any suitable container or receptacle with a sonolucent medium, for example a physiologic salt solution, and hook the calibration device in accordance with the invention onto the upper rim of the receptacle. Since the fiducials of the calibration device are arranged in a known spatial position relative to the tracking markers, the exact spatial position of the echogenic fiducials can be determined by means of a tracking system configured to detect the tracking markers. Similarly, the ultrasound probe can comprise tracking markers which can be detected by the tracking system, such that the relative position of the ultrasound probe and the fiducials can also be determined. Once the relative position of the ultrasound probe and the fiducials is known, it is possible to check whether the position of the fiducials as shown on the ultrasound image generated by the ultrasound probe matches the fiducial position determined via the tracking system.

While the method explained above is used for "static" calibration, the invention also offers a way of performing "dynamic" calibration.

In order to determine the time delay of the ultrasound image, the calibration device is moved within the container, thereby changing the position of the fiducials. Since the tracking system will determine any positional change in real time, a comparison between the fiducial position as determined via the tracking system and the fiducial position as determined via the ultrasound probe allows the time delay of the ultrasound image to be calculated.

A marker device can for example be a reference star or a pointer or a single tracking marker or a plurality of (individual) markers which are then preferably in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

A "reference star" refers to a device with a number of tracking markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star in particular features a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

The present invention is also applicable to a navigation system for computer-assisted surgery. This navigation system preferably comprises the aforementioned computer for processing the data provided in accordance with the data processing method as described in any one of the preceding embodiments. The navigation system preferably comprises a detection device and/or tracking system for detecting the position of the detection points and/or tracking markers which represent the main points and auxiliary points, in order to generate detection signals and to supply the generated detection signals to the computer, such that the computer can determine the absolute main point data and absolute auxiliary point data on the basis of the detection signals received. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, in particular a medical and/or surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

In the following, the invention is described with reference to the enclosed figures which represent preferred embodiments of the invention. The scope of the invention is not however limited to the specific features disclosed in the figures.

FIGS. 1A to 1D show four different side views of a preferred embodiment of the calibration device in accordance with the invention.

Figure 2B:
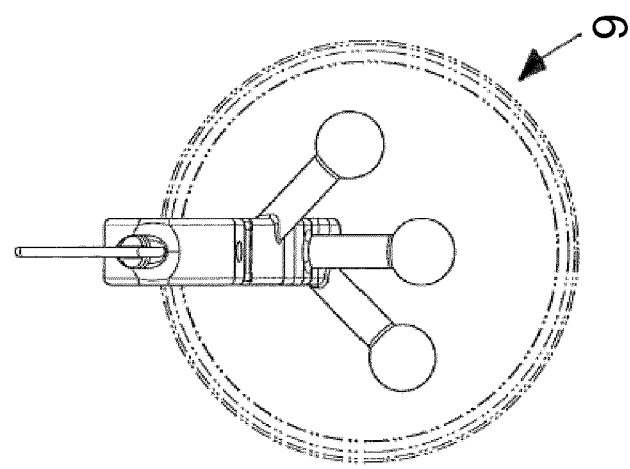
FIGS. 2A and 2B show the calibration device of FIGS. 1A to 1D together with a cup-shaped receptacle in a side view and top view, respectively.

As shown in FIGS. 1A to 1D, the calibration device in accordance with the invention comprises an elongated body portion 1 with three spherical fiducials 2 connected to it. Each of the fiducials 2 is connected to the body portion 1 via a rigid arm, wherein each of the arms extends in a direction perpendicular to the longitudinal axis of the body portion 1. FIG. 1D also shows that the arms extend in different directions so as to increase the distance between the fiducials 2. The body portion 1 also comprises two rated breaking features 6, one at the point of attachment between the distal fiducial 2 and the middle fiducial 2 and one at the point of attachment between the middle fiducial 2 and the proximal fiducial 2. Each of the rated breaking features 6 allows the part of the body portion 1 lying distally with respect to the breaking feature 6 to be broken off. The body portion 1 also comprises indication marks for each of the fiducials 2 which indicate the depth of the corresponding fiducials 2 below the watermark 8. The watermark 8 indicates the level to which the calibration device has to be submerged in a sonolucent medium in order to obtain the best possible result and to reach the depth indication provided by the indication marks printed on the body portion 1. A mounting portion 5 is connected to the body portion 1 and exhibits a hook-like shape with an opening which faces in a direction substantially parallel to the longitudinal axis of the body portion 1, although it may be seen that the opening and the parallel side walls of the hook extend at a certain angle relative to the longitudinal axis of the body portion 1, the reason being that this shape of the mounting portion 5 keeps the fiducials 2 away from the receptacle wall onto which the mounting portion 5 has been hooked. This is shown in more detail in FIGS. 2A and 2B.

A marker portion 3 of the calibration device is connected to the top of the mounting portion 5, wherein a handle portion 7 which is designed to be grasped by a person is arranged between the marker portion 3 and the mounting portion 5 and connects the mounting portion 5 and the marker portion 3 to each other. The marker portion 3 comprises three tracking markers 4 which can be detected by an optical tracking system (not shown) in order to determine the spatial position of the calibration device.

As can also be seen from FIGS. 1A to 1D, the ultrasound calibration device in accordance with the present invention is formed as an integral device comprising only one part which can be made from a plastic material, in particular from an injection-moulded plastic material. However, it is also conceivable for the calibration device to comprise two or more separate parts which are made from the same or from different materials and connected to each other.

Figure 2A:
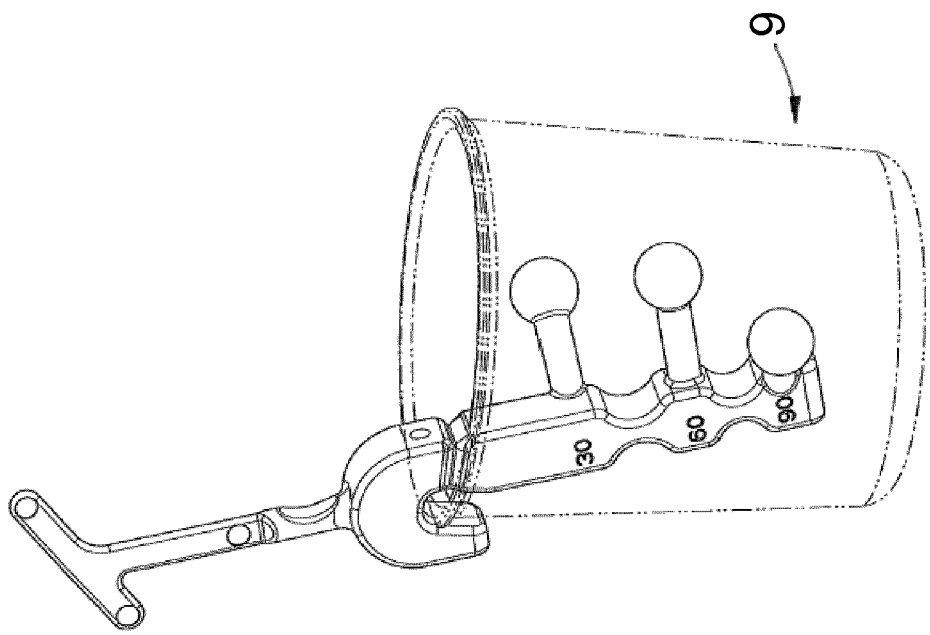

FIGS. 2A and 2B show the calibration device in accordance with the invention together with a receptacle 9 such as can be used with and form part of the present invention and which can be provided together with the calibration device, preferably as a disposable item made from a plastic material.

The invention claimed is:

1. An ultrasound calibration device, comprising:
   a body portion having one or more echogenic fiducials, the body portion being configured to be submerged together with the one or more echogenic fiducials into a sonolucent medium;
   a hook-shaped mounting portion extending from the body portion, the mounting portion being configured to be hooked onto an upper rim of a container, such that the body portion extends downwards into the container; and
   a marker portion connected to the mounting portion having at least one tracking marker which is configured to be detected by a medical tracking system.

2. The calibration device according to claim 1, wherein the mounting portion has an opening which points in a direction along a side of the body portion.

3. The calibration device according to claim 1, wherein the body portion has a longitudinal shape, and wherein the one or more echogenic fiducials include a plurality of echogenic fiducials, which are successively arranged along a side of the body portion.

4. The calibration device according to claim 3, wherein the body portion comprises at least one rated breaking feature between at least two of the plurality of echogenic fiducials.

5. The calibration device according to claim 1, further comprising a handle portion arranged between the marker portion and the mounting portion.

6. The calibration device according to claim 1, wherein the calibration device is made from a plastic material.

7. The calibration device according to claim 1, wherein the calibration device is formed as one integral part.

8. The calibration device according to claim 1, further comprising a connection interface,
   wherein the marker portion is attached to at least one of the body portion or the mounting portion via the connection interface which allows the marker portion to be attached to the calibration device.

9. The calibration device according to claim 1, wherein at least part of the calibration device exhibits an overall density which is equivalent to a density of a physiologic salt solution.

10. The calibration device according to claim 1, further comprising a mark at a predetermined distance to the at least one fiducial which indicates an extent to which the calibration device is to be submerged.

11. The calibration device according to claim 1, wherein the calibration device is a sterilised and disposable item.

12. An ultrasound calibration system, comprising a calibration device according to claim 1 and a container which is configured to be filled with a fluid and shaped so as to accommodate the calibration device.

13. A method for calibrating an ultrasound probe, comprising steps of:
    filling a container with a sonolucent medium;
    placing an ultrasound calibration device comprising:
       a body portion having at least one echogenic fiducial, the body portion being configured to be submerged together with at least one echogenic fiducial into a sonolucent medium;
       a hook-shaped mounting portion extending from the body portion, the mounting portion being configured to be hooked onto an upper rim of the container, such that the body portion extends downwards into the container, and
       a marker portion connected to the mounting portion and having at least one tracking marker which is configured to be detected by a medical tracking system, wherein the ultra-sound calibration device is placed with the hooked-shaped mounting portion being hooked onto an upper rim of the container; and comparing, with the aid of a medical navigation system, a calculated position of at least one fiducial with a determined position of the at least one fiducial which is determined using a tracked ultrasound probe wherein the position of the at least one fiducial is calculated using a virtual model of the calibration device and a tracking system which detects the spatial position of the at least one tracking marker.

14. The method according to claim 13, further comprising steps of:

grasping and moving the calibration device within the container;

determining, by utilizing a medical navigation system, a time delay of an ultrasound image by comparing the calculated position of the at least one fiducial with the determined position of the at least one fiducial while the calibration device is being moved.

15. The method according to claim 13, wherein the sonolucent medium is a physiologic salt solution.

16. An ultrasound calibration system, comprising:

a receptacle configured to be filled with a fluid, the receptacle comprising an upper rim; and an ultrasound calibration device, comprising:

a body portion having at least one echogenic fiducial, the body portion being configured to be submerged together with at least one echogenic fiducial into a sonolucent medium contained in the receptacle;

a hook-shaped mounting portion extending from the body portion, the mounting portion being configured to be hooked onto the upper rim of the receptacle, such that the body portion extends downwards into the receptacle; and a marker portion connected to the mounting portion and having at least one tracking marker which is configured to be detected by a medical tracking system.

17. The ultrasound calibration system of claim 16, wherein the receptacle is cup-shaped.

\* \* \* \* \*